United States Patent [19]
Wong et al.

[11] Patent Number: 6,017,511
[45] Date of Patent: Jan. 25, 2000

[54] GLYCOPEPTIDE-CHELATOR CONJUGATES

[75] Inventors: Ernest Wong, Etobicoke; Theresa Fauconnier, Toronto; Tam Nguyen, Scarborough; Alfred Pollak, Toronto; Suman Rakhit, Mississauga, all of Canada

[73] Assignee: Resolution Pharmaceuticals Inc., Mississauga, Canada

[21] Appl. No.: 08/865,965

[22] Filed: May 30, 1997

[51] Int. Cl.[7] .......................... A61K 51/00; A61M 36/14
[52] U.S. Cl. ................. 424/1.69; 424/1.11; 424/9.1; 424/1.65; 530/300; 530/328; 530/329; 530/330; 534/7; 534/10
[58] Field of Search .................. 424/1.11, 1.65, 424/1.69, 9.1, 1.53; 530/300, 324–330, 391.5; 534/7, 10–16; 540/465, 474, 450; 548/400; 546/1

[56] References Cited

U.S. PATENT DOCUMENTS

| | | | |
|---|---|---|---|
| 4,670,258 | 6/1987 | Harris et al. | 424/1.11 |
| 5,425,935 | 6/1995 | Solanki | 424/1.65 |
| 5,552,525 | 9/1996 | Dean | 530/326 |
| 5,569,745 | 10/1996 | Goodbody et al. | 530/328 |
| 5,662,885 | 9/1997 | Pollak et al. | 424/1.69 |

OTHER PUBLICATIONS

The Merck Index, Entry #9836 Vancomycin.

Schafer et al., Structure, 1996, vol. 4, No. 12, 1509–1515 "Crystal Structure of Vancomycin".

Sundram et al., J. Org. Chem., 1995, 60, 1102–1103 "General and Efficient Method for the Solution–and Solid–Phase Synthesis of Vancomycin Carboxamide Derivatives".

Shi et al., J. Am. Chem. Soc., 1993, 115, 6482–6486 "Catalysis of Carbamate Hydrolysis by Vancomycin and Semisynthetic Derivatives".

Nieto et al., Biochem J., 1971, 123, 773–787 "Physiochemical Properties of Vancomycin and Iodovancomycin and their Complexes with Diacetyl–L–lysyl–D–alanyl–D–alanine".

Perkins et al., Biochem J., 1970, 116, 83–92 "The Preparation of Iodinated Vancomycin and its Distribution in Bacteria Treated with the Antibiotic".

Wong et al (1997), Inorganic Chemistry, vol. 36, No. 25, pp. 5799–5808, "Rhenium(V) and Technetium(V) Oxo Complexes of an N2N'S peptidic Chelator: Evidence of Interconversion between the Syn and Anti Conformations".

*Primary Examiner*—Jose' G. Dees
*Assistant Examiner*—Dameron Jones
*Attorney, Agent, or Firm*—Nikaido Marmelstein Murray & Oram, LLP

[57] ABSTRACT

A peptide-chelator conjugate that is useful for imaging sites of inflammation in humans comprises a metal chelator coupled to a glycopeptide antibiotic. The metal chelator and the glycopeptide are coupled by a linking group. The linking group may be the divalent radical $NH-(CH_2)_3-NH$. Alternatively the linking group may be $\beta Ala_3LysGly$-OH and the glycopeptide may be coupled to the $N^\epsilon$ of Lys. A method of imaging a site of inflammation is also provided. The method comprises the step of administering a diagnostically effective amount of a composition comprising a glycopeptide-chelator conjugate comprising a metal chelator coupled to a glycopeptide antibiotic. The glycopeptide-chelator conjugate is in a form complexed with a diagnostically useful metal or an oxide or nitride thereof.

14 Claims, No Drawings

GLYCOPEPTIDE-CHELATOR CONJUGATES

FIELD OF THE INVENTION

This invention is in the field of diagnostic imaging, and relates to a glycopeptide targeting agent useful for targeting sites of inflammation.

BACKGROUND OF THE INVENTION

The art of diagnostic imaging exploits targeting agents that in binding or localizing sites selectively within the body, help to resolve the image of diagnostic interest. Monoclonal antibodies for example have been developed to have high affinity and specificity for particular cancer cells and therefore are useful for imaging tumours. Despite high affinity and specificity, antibodies do not provide ideal imaging agents since they are costly to produce on a commercial scale as well as their poor labelling characteristics. In particular, metal labels tend to bind at numerous low-affinity binding sites on antibodies and are released in vivo resulting in undesirable accumulation of the label at non-target sites. An alternative targeting agent to antibodies are small receptor binding peptides. Peptides offer the advantage of efficient labelling facilitated by conjugation to various chelating molecules. Other advantages of peptides over antibodies is their ease of synthesis, rapid tissue penetration and rapid clearance from the body.

In light of the difficulties associated with antibodies, it would be desirable to provide a glycopeptidic targeting agent capable of localizing at sites of inflammation while not having substantial accumulation in non-target tissue.

SUMMARY OF THE INVENTION

Glycopeptide-chelator conjugates are provided that when labelled with a traceable metal are useful for diagnostic imaging of sites of inflammation. The glycopeptide component is selected from glycopeptide antibiotics and derivatives thereof that are capable of targetting sites of inflammation, particularly those caused by bacterial infection, while the chelator component serves as a labelling site for metals, in particular radionuclide metals such as technetium-99m.

According to an aspect of the invention, there are provided glycopeptide-chelator conjugates in which the glycopeptide antibiotic Vancomycin is coupled at its COOH-terminus to a metal chelator.

In a particular embodiment of the present invention, the metal chelator component of the conjugate is of the formula I:

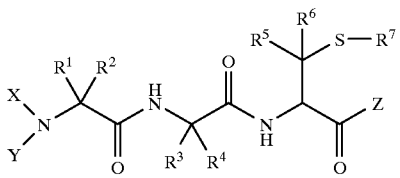

(I)

wherein

X is a linear or branched, saturated or unsaturated $C_{1-4}$alkyl chain that is optionally interrupted by one or two heteroatoms selected from N, O and S; and is optionally substituted by one or more substituents selected from halogen, hydroxyl, amino, carboxyl, $C_{1-4}$alkyl, aryl and C(O)Z;

Y is H or a substituent defined by X;

X and Y may together form a 5- to 8-membered saturated or unsaturated heterocyclic ring optionally substituted by one or more substituents selected from halogen, hydroxyl, amino, carboxyl, oxo, $C_{1-4}$alkyl, aryl and C(O)Z;

$R^1$ through $R^4$ are selected independently from H; carboxyl; $C_{1-4}$alkyl; $C_{1-4}$alkyl substituted with a substituent selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z;

$R^5$ and $R^6$ are selected independently from H; carboxyl; amino; $C_{1-4}$alkyl; $C_{1-4}$alkyl substituted by a substituent selected from hydroxyl, carboxyl and amino; and C(O)Z;

$R^7$ is selected from H and a sulfur protecting group; and

Z is selected from hydroxyl, alkoxy, an amino acid residue, and a linking group.

According to an aspect of the invention, the glycopeptide-chelator conjugates are provided in combination with a diagnostically useful metal or an oxide or nitride thereof.

According to another aspect of the present invention, there is provided a method of imaging a site of inflammation in a mammal, comprising the step of administering a diagnostically effective amount of a composition comprising a glycopeptide-chelator conjugate in which the glycopeptide antibiotic vancomycin is coupled at its COOH-terminus to a metal chelator which is complexed to a diagnostically useful metal or an oxide or nitride thereof.

DETAILED DESCRIPTION OF THE INVENTION

The invention provides glycopeptide-chelator conjugates that when complexed with a diagnostically useful metal are useful for imaging sites of inflammation. The glycopeptide-chelator conjugate, also referred to as "conjugate", incorporates a glycopeptide coupled at its COOH-terminus to any metal chelator, the glycopeptide component consisting of the glycopeptide antibiotic vancomycin hereinafter referred to as "the glycopeptide". In an embodiment of the present invention, the glycopeptide is coupled to the metal chelator (I) illustrated above which is disclosed in PCT application WO96/03427, published Feb. 8, 1996, incorporated herein by reference.

The terms defining the variables $R^1$–$R^7$ and X, Y and Z as used hereinabove in formula (I) have the following meanings:

"alkyl" refers to a straight or branched $C_1$–$C_8$ chain and includes lower $C_1$–$C_4$ alkyl;

"alkoxy" refers to straight or branched $C_1$–$C_8$ alkoxy and includes lower $C_1$–$C_4$ alkoxy;

"thiol" refers to a sulfhydryl group that may be substituted with an alkyl group to form a thioether;

"sulfur protecting group" refers to a chemical group that is bonded to a sulfur atom and inhibits oxidation of sulfur and includes groups that are cleaved upon chelation of the metal. Suitable sulfur protecting groups include known alkyl, aryl, acyl, alkanoyl, aryloyl, mercaptoacyl and organothio groups.

"linking group" refers to a chemical group that serves to couple the glycopeptide to the chelator while not adversely affecting either the targetting function of the peptide or the metal binding function of the chelator. Suitable linking groups include alkyl chains; alkyl chains optionally substituted with one or more substituents and in which one or more carbon atoms are optionally replaced with nitrogen, oxygen or sulfur atoms.

Other suitable linking groups include those having the formula $A^1$-$A^2$-$A^3$ wherein $A^1$ and $A^3$ are independently selected from N, O and S; and $A^2$ includes alkyl optionally substituted with one or more substituents and in which one or more carbon atoms are optionally replaced with nitrogen, oxygen or sulfur atoms; aryl optionally substituted with one or more substituents; and heteroaryl optionally substituted with one or more substituents. Still other suitable linking groups include amino acids and amino acid chains functionalized with one or more reactive groups for coupling to the glycopeptide and/or chelator. In one embodiment, the linking group is a peptide of 1 to 5 amino acids and includes, for example, chains of 1 or more synthetic amino acid residues such as β-Alanine residues. In another embodiment, the linking group is NH-alkyl-NH.

"metal chelator" refers to a molecule that forms a stable complex with a traceable metal atom under physiological conditions in that the metal remains bound to the conjugate in vivo. For diagnostic imaging purposes, a chelator is a compound which has a reactive functional group for labelling by a radionuclide and, on binding to a radionuclide metal, forms a complex that is stable under physiological conditions. Many chelator compounds have been developed for this purpose. Commonly used chelating agents include, for example, DTPA (diethylenetriaminepentaacetic acid) and ethylene diamine tetracetic acid (EDTA). Other chelators appropriate to link a radionuclide metal label to a compound in accordance with the present invention are described in standard texts such as *Advanced Inorganic Chemistry, 4th edition,* 1980, F. A. Cotton and G. Wilkinson, John Wiley & Sons. However, as will be appreciated by those of skill in the art, the most suitable metal chelating agent will vary with the metal to be chelated, e.g. depending on its particular coordination. Chelators suitable specifically for linking $^{99m}$Tc to cell-associating compounds in accordance with the present invention typically present, as a metal coordinating configuration, a combination of four nitrogen and sulfur metal-coordinating atoms.

Examples include compounds having $N_4$, $N_3S$ and $N_2S_2$ conformations. However, such chelators may incorporate other metal-coordinating atoms including oxygen, phosphorous and selenium. In one embodiment of the present invention, $N_3S$ chelators, such as those described in co-pending U.S. application Ser. Nos. 08/171,737, 08/279,155 and 08/299,636, the contents of each of which are incorporated herein by reference, are used to prepare the present conjugates. In another embodiment, $N_2S_2$ chelators, such as those described in co-pending U.S. application Ser. No. 08/116,504, also incorporated herein by reference, are used to prepare conjugates. In a specific embodiment of the present invention, and as set out in the specific examples herein, one chelator used to prepare peptide conjugates is dimethyl-glycine-serine-cysteine(Acm). Reference can be made to FIG. 1 for the amino acid sequence of a specific conjugate which incorporates this chelator.

In preferred embodiments of the invention, the chelators conform to the above formula (I) in which: X and Y each are methyl, $R^1$, $R^2$, $R^4$, $R^5$ and $R^6$ each are H; $R^3$ is $CH_2OH$; $R^7$ is acetamidomethyl; and Z is a linking group selected from $NH(CH_2)_3NH$ and a peptide chain consisting of one to three amino acid residues;

A conjugate may incorporate a metal chelator component that is peptidic ie. compatible with solid-phase peptide synthesis.

Glycopeptide-chelator conjugates of the invention may be prepared by various methods depending upon the chelator chosen. The peptide portion of the conjugate is most conveniently prepared by techniques generally established in the art of peptide synthesis, such as the solid-phase approach. Solid-phase synthesis involves the stepwise addition of amino acid residues to a growing peptide chain that is linked to an insoluble support or matrix, such as polystyrene. The C-terminus residue of the peptide is first anchored to a commercially available support with its amino group protected with an N-protecting agent such as a t-butyloxycarbonyl group (tBoc) or a fluorenylmethoxycarbonyl (FMOC) group. The amino protecting group is removed with suitable deprotecting agents such as TFA in the case of tBOC or piperidine for FMOC and the next amino acid residue (in N-protected form) is added with a coupling agent such as dicyclocarbodiimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF). The glycopeptide portion can be obtained commercially or can be prepared by techniques well known in the art.

Conjugates may further incorporate a linking group component that serves to couple the peptide to the chelator while not adversely affecting either the targetting function of the peptide or the metal binding function of the chelator.

Glycopeptide and chelator components are coupled to form a conjugate by reacting an appropriate functional group of the chelator or linker with an appropriate functional group of the glycopeptide. For example, the free carboxyl group of the glycopeptide vancomycin may be coupled to an amino group of the conjugate or linker.

In accordance with one aspect of the invention, glycopeptide-chelator conjugates incorporate a diagnostically useful metal capable of forming a complex. Suitable metals include radionuclides such as technetium and rhenium in their various forms such as $^{99m}TcO^{3+}$, $^{99m}TcO_2^+$, $ReO^{3+}$ and $ReO_2^+$. Incorporation of the metal within the conjugate can be achieved by various methods common in the art of coordination chemistry. When the metal is technetium-99m, the following general procedure may be used to form a technetium complex. A peptide-chelator conjugate solution is formed initially by dissolving the conjugate in aqueous alcohol such as ethanol. The solution is then degassed to remove oxygen then thiol protecting groups are removed with a suitable reagent, for example with sodium hydroxide and then neutralized with an organic acid such as acetic acid (pH 6.0–6.5). In the labelling step, a stoichiometric excess of sodium pertechnetate, obtained from a molybdenum generator, is added to a solution of the conjugate with an amount of a reducing agent such as stannous chloride sufficient to reduce technetium and heated. The labelled conjugate may be separated from contaminants $^{99m}TcO_4^-$ and colloidal $^{99m}TcO_2$ chromatographically, for example with a C-18 Sep Pak cartridge.

In an alternative method, labelling can be accomplished by a transchelation reaction. The technetium source is a solution of technetium complexed with labile ligands facilitating ligand exchange with the selected chelator. Suitable ligands for transchelation include tartarate, citrate and heptagluconate. In this instance the preferred reducing reagent is sodium dithionite. It will be appreciated that the conjugate may be labelled using the techniques described above, or alternatively the chelator itself may be labelled and subsequently coupled to the peptide to form the conjugate; a process referred to as the "prelabelled ligand" method.

Another approach for labelling conjugates of the present invention involves techniques described in a co-pending U.S. application Ser. No. 08/152,680 filed Nov. 16, 1993, incorporated herein by reference. Briefly, the glycopeptide-chelator conjugates are immobilized on a solid-phase support through a linkage that is cleaved upon metal chelation. This is achieved when the chelator is coupled to a functional group of the support by one of the complexing atoms. Preferably, a complexing sulfur atom is coupled to the support which is functionalized with a sulfur protecting group such as maleimide.

When labelled with a diagnostically useful metal, glycopeptide-chelator conjugates of the present invention can be used to detect sites of inflammation by procedures established in the art of diagnostic imaging. A conjugate labelled with a radionuclide metal such as technetium-99m may be administered to a mammal by intravenous injection in a pharmaceutically acceptable solution such as isotonic saline. The amount of labelled conjugate appropriate for administration is dependent upon the distribution profile of the chosen conjugate in the sense that a rapidly cleared conjugate may be administered in higher doses than one that clears less rapidly. Unit doses acceptable for imaging inflammation are in the range of about 5–40 mCi for a 70 kg individual. In vivo distribution and localization is tracked by standard scintigraphic techniques at an appropriate time subsequent to administration; typically between 30 minutes and 180 minutes depending upon the rate of accumulation at the target site with respect to the rate of clearance at non-target tissue.

The following examples are presented to illustrate certain embodiments of the present invention.

Materials

Vancomycin-HCl, 1,3-diaminopropane, dimethylsulfoxide (DMSO), N,N-dimethylformamide, (DMF) 2,3,5,6-tetrafluorophenol (TFP), 1-[3-(dimethylamino)propyl]3-ethylcarbodiimide chloride (EDC), tin(II) chloride and sodium gluconate were purchased from Aldrich Chemicals Inc. 2-(1H-benzotriazol-1-yl)-1,1,3,3-tetramethyl-uronium hexafluorophosphate (HBTU), 1-hydroxybenzotriazole (HOBT), and diiso-propylethylamine (DIEA) were purchased from Applied Biosystems Inc. Dimethylglycine-serine-cysteine-glycine was purchased from American Peptide Inc. All chemicals were used as received.

Instrumentation

Mass spectra (electrospray) were obtained on a Sciex API#3 mass spectrometer in the positive ion detection mode. HPLC analyses and purifications were made on a Beckman System Nouveau Gold chromatographic system with a Waters 4 mm radial pak C-18 column. During analytical HPLC analysis, the mobile phase were changed from 100% 0.1% aqueous trifluoroacetic acid to 20% acetonitrile containing 0.1% trifluoroacetic acid over 40 minutes at a flow rate of 2 mL/min. The HPLC analyses were monitored with a UV detector set at 215 nm. HPLC analyses of the $^{99m}$Tc samples were made on a Beckman System Gold chromatographic system with a Vydac 4.6 mm radial pak C-18 column. The mobile phase was changed from 100% 0.1% aqueous trifluoroacetic acid to 70% acetonitrile containing 0.1% trifluoroacetic acid over 25 minutes at a flow rate of 1 mL/min. The HPLC analyses of the $^{99m}$Tc samples were monitored with a UV detector set at 215 nm and a radiometric gamma dectector.

EXAMPLE 1

Preparation of Glycopeptide-Chelator Conjugate DimethylGly-Ser-Cys(Acm)-Gly-NH(CH$_2$)$_3$NH-Vancomycin [SEQ ID NO:1] of the Formula (IA)

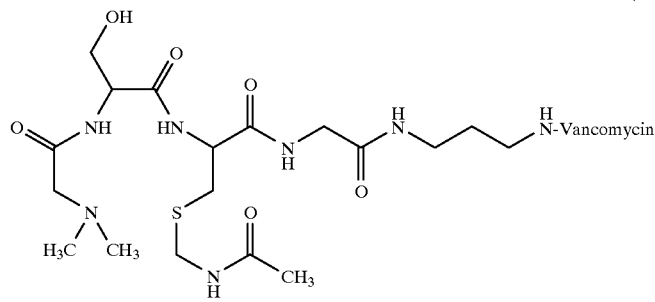

(IA)

Two methods were used to prepare the conjugate of Formula (IA). The two methods differ in the sequence in which the the glycopeptide vancomycin, the linker 1,3-diaminopropane and the chelator dimethylGly-Ser-Cys (ACM)-Gly [SEQ ID NO:2] are combined to form the conjugate of Formula (IA).

Method A (i) Synthesis of the Linker-Glycopeptide Portion: NH$_2$(CH$_2$)$_3$NH-Vancomycin Vancomycin.HCl (210.9 mg, 0.142 mmoles) was dissolved in 1 mL of DMSO and 1 mL of DMF. The solution was cooled to 0° C. 1,3-diaminopropane (21.0 mg, 0.284 mmoles) was added to the solution. To this solution was added 0.45 M HBTU/HOBT in DMF (0.448 mL, 0.202 mmoles), and DIEA (69.5 mg, 0.538 mmoles). The solution was stirred under Ar at 0° C. for 1 hour. The solution was then stirred under Ar at room temperature for 24 hours. The solution was added dropwise to tert-butyl methyl ether at 0° C., resulting in the formation of white precipitate. The precipitate was collected by centrifugation and analyzed by HPLC. The crude product was purified by HPLC. Yield: 47 mg (22%). Mass spectrum (electrospray): m/z=1505 ([MH]$^+$, [C$_{69}$H$_{84}$Cl$_2$N$_{11}$O$_{23}$]$^+$), m/z=753 ([MH$_2$]$^{2+}$, [C$_{69}$H$_{86}$Cl$_2$N$_{11}$O$_{23}$]$^{2+}$). HPLC retention time: R$_t$=26.4 min.

(ii) Synthesis of the Conjugate of Formula (IA)

DimethylGly-Ser-Cys(Acm)-Gly [SEQ ID NO:2] (5.5 mg, 0.013 mmoles) was dissolved in 90% aqueous acetonitrile. TFP (4.3 mg, 0.026 mmoles) and EDC (5.0 mg, 0.026 mmoles) were dissolved in 90% aqueous acetonitrile and added to this solution. The solution was stirred and heated under Ar at 40–45° C. for 1 hour. NH$_2$(CH$_2$)$_3$NH-Vancomycin (4.7 mg, 0.0031 mmoles) perpared above was dissolved in HCO$_3^-$/CO$_3^{2-}$ buffer and added to this solution. The pH was adjusted to 9 using 1 M NaOH. The solution was stirred and heated under Ar at 40–45° C. for an additional hour. The crude product was purified by HPLC. Yield: 15.9 mg (64%). Mass spectrum (electrospray): m/z= 1908 ([M]$^+$, [C$_{84}$H$_{111}$Cl$_2$N$_{17}$O$_{28}$S$_1$]). HPLC retention time: R$_t$=29.3 min.

Method B (i) Synthesis of the Chelator-Linker Portion: DimethylGly-Ser-Cys(Acm)-Gly-NH(CH$_2$)$_3$NH$_2$ [SEQ ID NO:3]

DimethylGly-Ser-Cys(Acm)-Gly [SEQ ID NO:3] (75 mg, 0.18 mmol) was dissolved in 9:1 acetonitrile:H$_2$O (0.5 mL). TFP was added (44 mg, 0.27 mmol), followed by EDC (51 mg, 0.27 mmol). The solution was heated at 40° C. for 1 h, at which time 1,3-diaminopropane (59 µL, 0.71 mmol) was added. The solution was heated for 1 h more at 40° C. The acetonitrile was evaporated under reduced pressure (1 mm Hg, 30° C.), and the remaining H$_2$O was removed by lyophilization. The pale yellow oily crude product was purified by HPLC. Yield: 56 mg, 65%. Mass spectrum (electrospray): m/z=478 ([MH]$^+$, [C$_{18}$H$_{38}$N$_8$O$_5$S$_1$]). HPLC retention time: R$_t$=6.9 min.

(ii) Synthesis of the Conjugate of Formula (IA)

DimethylGly-Ser-Cys(Acm)-Gly-NH(CH$_2$)$_3$NH$_2$ [SEQ ID NO:3] (25 mg, 0.05 mmol) perpared above was dissolved in dry DMF (200 µL). Vancomycin-HCl was added (41 mg, 0.03 mmol). Dry DMF (0.5 mL) and dry DMSO (200 µL) were added. The mixture was stirred under argon for 1 h, during which time the vancomycin dissolved. To this solution was added 0.45 M HBTU/HOBT in DMF (93 µL, 0.04 mmol), followed by DIEA (24 µL, 0.14 mmol). The solution was stirred under argon for 16 h, at which time it was diluted with acetone (30 mL) to produce a white solid. The solid was collected by centrifugation and analyzed by HPLC. The crude product was purified by HPLC. Yield: 43 mg, 75%; Mass spectrum (electrospray): m/z=955 ([MH$_2$]$^+$, [C$_{84}$H$_{113}$Cl$_2$N$_{17}$O$_{28}$S$_1$]), m/z=637 ([MH$_3$]$^+$, [C$_{84}$H$_{114}$Cl$_2$N$_{17}$O$_{28}$S$_1$]). HPLC retention time: R$_t$=28.9 min.

EXAMPLE 2

Synthesis of the $^{99m}$Tc Complex of the Conjugate of Formula (IA)

The conjugate of Formula (IA) (260 mg, 136 mmoles) was dissolved in 200 mL of saline. Na[$^{99m}$TcO$_4$] (10 mCi) was added to the solution, followed by tin(II) chloride (7.5×10$^3$ mg, 39 mmoles), sodium gluconate (1.3×10$^3$ mg, 5.8 mmoles), and 20 µL of 0.1 M NaOH. The solution was incubated at 40° C. for 1 hour. In the synthesis of the $^{99m}$Tc-conjugate of Formula (IA) complex, the acetoamidomethyl protection group was displaced from the cysteine thiolate. The $^{99m}$Tc-conjugate complex was analyzed by HPLC. A radiochemical yield of 88% was achieved. HPLC retention time: $^{99m}$Tc-Conjugate of Formula (IA) R$_t$=17.4 min (radiometric gamma detector); R$_t$=16.2 min (UV detector).

EXAMPLE 3

Preparation of Glycopeptide-Chelator Conjugate DimethylGly-Ser-Cys(Acm)-(βAla)$_3$-Lys(N$^\epsilon$-Vancomycin)-Gly-OH [SEQ ID NO:4] of the Formula (IB)

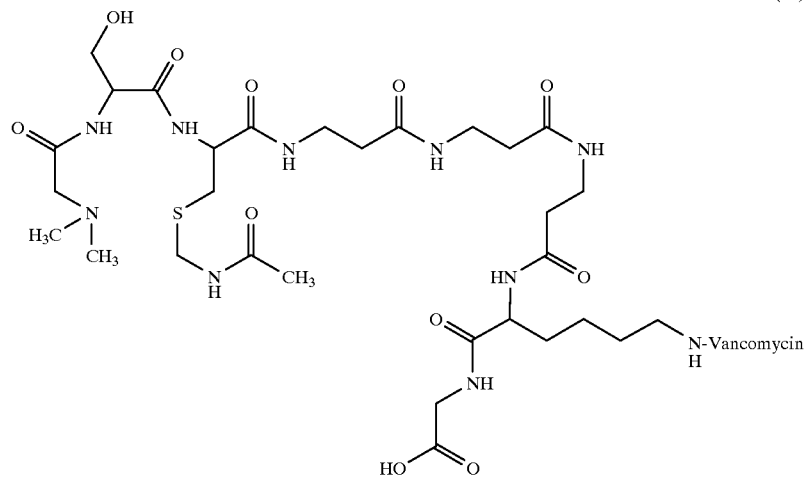

(IB)

(A) Synthesis of dimethylGly-Ser(t-Butyl)-Cys(Acm)-(βAla)$_3$-Lys-Gly-sasrin resin [SEQ ID NO:5]

The peptidyl chelate-resin, dimethylGly-Ser(t-butyl)-Cys(Acm)-(βAla$_3$)-Lys(Dde)-Gly-sarsin resin [SEQ ID NO:6] was prepared as a single peptide chain on an ABI Peptide Synthesizer model 433A using FastMoc chemistry and preloaded resin. A FastMoc 1.0 mmol chemistry and preloaded Fmoc-glycine sasrin resin (0.7 mmol/g, 1.429 g) required three cartridges of every representative Fmoc amino acid derivatives (3*1.0 mmol). N,N-Dimethylglycine (3*1 mmol) was pretreated with 0.45 M HBTU/HOBT/DMF (3*1 mL) before inserted on the synthesizer. After completion of automatic synthesis, the resulting product was removed from the synthesizer, and dried under vacuum for 2 hours. The Lys(Dde) residue (2 g) was deprotected by two treatments of 5 minutes with 2% hydrazine/NMP. Subsequent NMP (5*10 mL), and DCM washes (5*10 mL) to afford the titled chelate-resin (1.73 g).

(B) Synthesis of dimethylGly-Ser-Cys(Acm)-(βAla$_3$)-Lys (N$^\epsilon$-Vancomycin)-Gly-OH [SEQ ID NO:4]

Method 1

The automatic synthesis of dimethylGly-Ser-Cys(Acm)-(βAla)$_3$-Lys(N$^\epsilon$-Vancomycin)-Gly-sasrin resin [SEQ ID NO:7] was continued using double coupling cycle of Fast-Moc 1.0 mmol chemistry on the preloaded dimethylGly-Ser (t-Butyl)-Cys(Acm)-(βAla$_3$)-Lys-Gly-sasrin resin [SEQ ID NO:5] (423 mg, 0.25 mmol) and an assembly of vancomycin at the N$^\epsilon$-lysine position. Vancomycin hydrochloride (2 equivalents, 0.50 mmol, 557 mg) was pre-dissolved in DMSO (100 mg of vancomycin/mL) and equally transferred to six amino acid cartridges. Each coupling module required three amino acid cartridges containing 1 equivalent of the vancomycin solution. During the activation and transfer modules, the vancomycin solution was activated by 0.45 M HBTU/HOBt/DMF (6*2.0 g) with additional 2 M DIEA/NMP (3 mL). Each coupling module of every equivalent of activated vancomycin (3 cartridges/equivalents) to the chain assembly was extended from 15 minutes to 5 hours by modifying 20 loops for the steps of vortex reaction vessel on in 25 seconds and of vortex reaction off in 5 seconds. After the synthesis finished, 520 mg of the resulting resin was obtained. The resin was treated with 2% TFA in DCM at room temperature for 30 minutes, and well washed with DCM. After the supernatant was removed, 50 mg (25 μmol) over 500 mg of the resulting resin was taken and treated with 10% TFA:water (95:5) in DCM at 0° C. for 30 minutes followed by stirring at room temperature for 3 hours. The supernatant was concentrated on rotovap at ambient temperature, precipitated in MTBE (30 mL), centrifuged, and lyophilized to yield the crude product (10 mg), HPLC R$_f$ 29.6 minutes, purity of 21%. Purification of the crude peptide and lyophilization afforded the titled vancomycin-chelate conjugate as a white pellet (2 mg, 25 μmol, 4%): HPLC R$_f$ 29.5 minutes, ES-MS (C$_{96}$H$_{127}$N$_{19}$O$_{34}$S$_1$Cl$_2$, m.w. 2194.15) m/z 1098 (M$^{+2}$), 732 (M$^{+3}$).

Method 2

The coupling reaction the peptidyl chelate-resin and vancomycin was also prepared off the synthesizer. The chelate-resin (0.25 mmol, 423 mg) was swollen in NMP (0.10 mmol/1 mL) at room temperature under argon for 30 minutes, added a solution of vancomycin hydrochloride (1.5 equivalents, 557 mg) in DMSO (94 μmol/1 mL), 0.45 M HBTU/HOBt/DMF (1.5 equivalents, 0.375 mmol, 835 μL), and 2.0 M DIEA/NMP (5.0 equivalents, 1.25 mmol, 625 μL). The suspension was vortexed for 16 hours and filtered. After the supernatant was discarded, the resulting resin was washed with NMP (10*10 mL), DMSO (2*5 mL), DCM (10*10 mL) and dried under vacuum. After being treated with 2% TFA in DCM at room temperature for 30 minutes and washed with DCM (5*10 mL), a 50-mg (24.5 μmol) portion of 510 mg the resulting resin was deprotected by 10% TFA:water (95:5) in DCM at 0° C. for 30 minutes followed by stirring at room temperature for 2 hours. The supernatant was concentrated on rotovap at ambient temperature, and precipitated in MTBE (30 mL), centrifuged, and lyophilized over 16 hours to yield the crude product (24 mg): HPLC R$_f$ 29.6 minutes, purity of 31%. Purification of the crude peptide and lyophilization afforded the titled conjugate as a white pellet (6 mg, 24.5 μmol, 11%): HPLC R$_f$ 29.7 minutes, ES-MS (C$_{96}$H$_{127}$N$_{19}$O34S$_1$Cl$_2$, m.w. 2194.15) m/z 1098 (M$^{+2}$), 732 (M$^{+3}$).

(C) Synthesis of dimethylGly-Ser(t-Butyl)-Cys(Acm)-(βA$_3$)-Lys(N$^\epsilon$-Vancomycin)-Gly-OH [SEQ ID NO:8]

2% TFA pre-treated dimethylGly-Ser(t-Butyl)-Cys(Acm)-(βAla$_3$)-Lys(N$^\epsilon$-Vancomycin)-Gly-sasrin resin [SEQ ID NO:9] (50 mg, 25 μmol) was obtained from method 1, and further reacted with 5% TFA in DCM at 2° C. for 4 hours. The supernatant was concentrated on rotovap at ambient temperature, and precipitated in MTBE (30 mL), followed by centrifugation and lyophilization over 16 hours to obtain the crude peptide (121 mg), HPLC R$_f$ 35.2 minutes, purity of 34%. Purification of the crude peptide (20 mg, 8.3 μmol) and lyophilization afforded the titled vancomycin-chelate(t-Butyl) conjugate as a white pellet (5 mg, 27%): HPLC: 35.5 minutes, ES-MS (C$_{100}$H$_{135}$N$_{19}$O$_{34}$S$_1$Cl$_2$, m.w. 2249.26) m/z 1126 (M$^{+2}$), 751 (M$^{+3}$).

EXAMPLE 4

Synthesis of the $^{99m}$Tc DimethylGly-Ser-Cys-(βAla$_3$)-Lys(N$^\epsilon$-Vancomycin)-Gly-OH [SEQ ID NO:4]

dmG-Ser-Cys(Acm)-βA$_3$-Lys(N$^\epsilon$-Vancomycin)-Gly-OH (100 μg, 48 μmol) was dissolved in 100 μL of saline. Na[$^{99m}$TcO$_4$] (10 mCi) was added to the solution, followed by tin(II) chloride (7.5×10$^3$ μg, 39 μmol) and sodium gluconate (1.3×10$^3$ μg, 5.8 μmol), and 20 μL of 0.1 M NaOH for buffering. The solution was incubated at 30° C. for 1 hour. The Acm protecting group of cysteine was displaced from the cysteine thiolate. HPLC analysis after 1 hour of incubation gave R$_f$ 17.25 minutes, 51.0% by radiometric gamma detector and R$_f$ 16.73 minutes by UV detector.

EXAMPLE 5

Binding of Conjugates to Bacteria

A. Filter Binding Assay

Frozen cultures of bacteria are stored in vials at −80° C. until use. To inoculate a fresh bacterial culture, the vial of bacteria is removed from the freezer and continually kept frozen by being placed on dry ice. A small amount is removed using a sterile wooden applicator and transferred to a 50 mL culture flask, with screw cap, containing 10 mL of broth medium. The culture is incubated at 37° C. on a shaker at 200 rpm overnight*. The various microorganisms or compounds and broth media used are:

*Note: *C. albicans* has a longer growth cycle than the other microorganisms and, therefore, the culture is incubated for 2 days. Also, the optimum growth temperature for *C. albicans* is 30° C. Zymosan and carrageenan do not have to be incubated overnight and can remain at room temperature.

*E. coli* (ATCC 25922)→Tryptic Soy Broth (TSB; Difco)

*S. aureus* (ATCC 25923)→TSB

*P. aeruginosa* (ATCC PAO-PR1)→TSB

*C. albicans* (ATCC 14053)→YM Broth (YMB; Difco)

Zymosan (Sigma)→YMB

Carrageenan (Sigma)→YMB

The cultures are then subcultured by removing 50–150 mL of the culture (O.D. dependent) and transferring to a 50 mL culture flask containing 20 mL broth. The subcultures are incubated at 37° C. or 30° C. until a growth concentration of 10$^8$ cfu (colony forming unit)/mL is reached. The concentration of each microorganism is determined by reading the optical density (O.D.) of the subculture using a spectrophotometer. The correlation between O.D. and growth of each microorganism has been previously established.

Once the proper O.D. has been reached, 10 mL of the subculture is transferred to a 15 mL culture flask and 1×10$^6$ cpm of Tc-99m-labelled compound is added. The flasks are incubated in a shaking water bath (200 rpm) at 37° C. A 10 mL zymosan suspension at 50 mg/mL and a 0.5% carrageenan mixture are also made. There is also a background which is a flask containing broth with no microorganism and to which the radioactivity is also added. At various time intervals, 200 mL of the cultures, suspensions, and the background is removed and filtered through 25 mm diam., 22 mm, cellulose acetate/nitrate, membrane filters (Millipore) using a Millipore vacuum manifold. The filters are washed 3× with 1 mL PBS. The filters are then assayed for radioactivity using a gamma well counter (Cobra II; Canberra Packard). The time intervals at which the cultures are sampled are:

0**, 30, 60, and 120 min. post-addition of the radiolabelled compound

**Note: Time 0 refers to immediately after addition of the radiolabelled compound The following results were obtained using vancomycin linked to two different chelators and labelled with Tc-99m:

TABLE I

Filter Binding Assay Results at 2 h

| Compound | Bacteria | | | | |
|---|---|---|---|---|---|
| | S. aureus | E. coli | C. albicans | P. aeruginosa | Zymosan |
| (IB) | 22% | 18% | 5% | — | 42% |
| (IA) | 48% | 31% | 21% | 25% | 35% |

B. Antimicrobial Assays

Fresh cultures of bacteria are made from frozen stock stored at −80° C. To inoculate a fresh culture, the stock is removed from the freezer and continually kept frozen by being placed on dry ice. A small amount is removed using a sterile wooden applicator and transferred to a 50 mL culture flask, with screw cap, containing 10 mL of broth medium. The culture is incubated at 37° C. on an orbital shaker at 200 rpm overnight. The various bacteria and broth media used are:

E. coli→TSB
S. aureus→TSB
P. aeruginosa→TSB

The following day, the cultures are subcultured by transferring 50–150 mL (O.D. dependent) to a new culture flask containing 20 mL broth. The subcultures are incubated at 37° C. on a shaker (200 rpm) and the bacteria are allowed to grow to mid-log phase. This is usually around $1 \times 10^8$ cfu/mL, determined by measuring the O.D. of the subculture. The correlation between O.D. and growth of each bacteria has been previously established.

Once the proper O.D. has been obtained, a 200- or 400-fold dilution is made of the subculture and 1 mL of this dilution is added to 1 mL of compound or antibiotic (i.e. 2-fold dilution) to give a final concentration of 0, 2, 4, 8, 16, 32, and 64 mg/mL compound or antibiotic. A 100-fold dilution is made from the control culture (0 mg/mL) and 100 mL samples (i.e. 1000-fold dilution) are plated onto a TSA (tryptic soy agar; Difco). The cultures are incubated overnight at 37° C. on an orbital shaker (200 rpm). The TSA plates are also incubated overnight at 37° C.

The following day, the cultures are examined for growth or turbidity. 100 mL samples (i.e. 10-fold dilution) of any of the cultures showing no turbidity, i.e. no growth, are plated onto TSA. The plates are incubated overnight at 37° C. and the number of cfu, if any, are counted. The control TSA plates are counted for the number of cfu for comparison with the culture plates.

MIC (minimal inhibitory concentration) is determined to be the lowest concentration at which growth of the bacteria is arrested. MBC (minimal bactericidal concentration) is determined to be the lowest concentration at which the bacteria are being killed.

The following results were obtained:

TABLE II

Results of the Antimicrobial Assay

| Compound | Dilution | Control | Concentration (mg/mL) | | | |
|---|---|---|---|---|---|---|
| | | | 8 | 16 | 32 | 64 |
| (IA) | 200-fold | $5.6 \times 10^5$ cfu/mL | too many to count | 80 cfu/mL | no growth | no growth |
| Vancomycin | 200-fold | $3.0 \times 10^5$ cfu/mL | too many to count | too many to count | 30 cfu/mL | no growth |
| | 400-fold | $1.3 \times 10^5$ cfu/mL | too many to count | 60 cfu/mL | no growth | no growth |

The MIC for the conjugate of Formula (IA) was determined to be between 16–32 mg/mL. The MBC for RP428 was found to 32 mg/mL. Table II illustrates that the MIC for vancomycin was also between 16–32 mg/mL and the MBC was found to be between 32–64 mg/mL. The antimicrobial assay was performed with S. aureus, E. coli, and P. aeruginosa for both RP428 and vancomycin. However, the conjugate of Formula (IA) and vancomycin was found to antimicrobial against only S. aureus at the concentrations tested.

We claim:

1. A peptide-chelator conjugate useful for imaging sites of inflammation comprising a metal chelator coupled to a glycopeptide antibiotic, the metal chelator and the glycopeptide being coupled by a linking group which is the divalent radical NH—(CH$_2$)$_3$—NH.

2. A peptide-chelator conjugate according to claim 1, wherein the metal chelator is coupled to the COOH terminus of the glycopeptide antibiotic.

3. A peptide-chelator conjugate according to claim 1, wherein the metal chelator is coupled to an amino group of the glycopeptide antibiotic.

4. A peptide-chelator conjugate useful for imaging sites of inflammation comprising a metal chelator coupled to a glycopeptide antibiotic, the metal chelator and the glycopeptide being coupled by a linking group wherein the linking group is one or more amino acid residues, the linking group being βAla$_3$LysGly-OH and the glycopeptide being coupled to the N$^\epsilon$ of Lys.

5. A peptide-chelator conjugate according to claim 1, wherein the metal chelator has the general Formula (I):

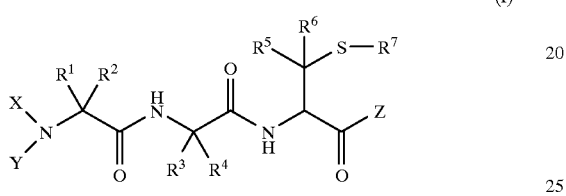

wherein
X is a linear or branched, saturated or unsaturated C$_{1-4}$alkyl chain that is optionally interrupted by one or two heteroatoms selected from N, O and S; and is optionally substituted by at least one group selected from the group consisting of halogen, hydroxyl, amino, carboxyl, C$_{1-4}$alkyl, aryl and C(O)Z;

Y is H or a substituent defined by X;

X and Y may together form a 5- to 8-membered saturated or unsaturated heterocyclic ring optionally substituted by at least one group selected from the group consisting of halogen, hydroxyl, amino, carboxyl, oxo, C$_{1-4}$alkyl, aryl and C(O)Z;

R$^1$ through R$^4$ are selected independently from the group consisting of H; carboxyl; C$_{1-4}$alkyl; C$_{1-4}$alkyl substituted with a group selected from the group consisting of hydroxyl, amino, sulfhydryl, halogen, carboxyl, C$_{1-4}$alkoxycarbonyl and aminocarbonyl; an alpha carbon side chain of a D- or L-amino acid other than proline; and C(O)Z;

R$^5$ and R$^6$ are selected independently from the group consisting of H; carboxyl; amino; C$_{1-4}$alkyl; C$_{1-4}$alkyl substituted by hydroxyl, carboxyl or amino; and C(O)Z;

R$^7$ is selected from H and a sulfur protecting group; and

Z is selected from the group consisting of hydroxyl, alkoxy, an amino acid residue, and a linking group.

6. A peptide-chelator conjugate according to claim 5, wherein the glycopeptide antibiotic is coupled to the metal chelator at Z.

7. A peptide-chelator conjugate according to claim 5, wherein the glycopeptide antibiotic is coupled to the metal chelator by a linking group at Z.

8. A peptide-chelator conjugate useful for imaging sites of inflammation comprising a metal chelator coupled to a glycopeptide antibiotic, the metal chelator having the general Formula (I):

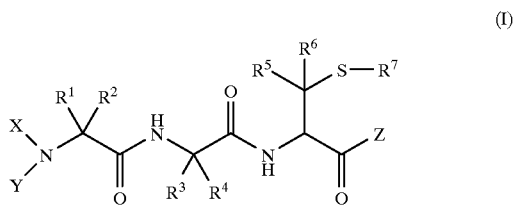

wherein

X is a linear or branched, saturated or unsaturated C$_{1-4}$alkyl chain that is optionally interrupted by one or two heteroatoms selected from N, O and S; and is optionally substituted by at least one group selected from halogen, hydroxyl, amino, carboxyl, C$_{1-4}$alkyl, aryl and C(O)Z;

Y is H or a substituent defined by X;

X and Y may together form a 5- to 8-membered saturated or unsaturated heterocyclic ring optionally substituted by at least one group selected from halogen, hydroxyl, amino, carboxyl, oxo, C$_{1-4}$alkyl, aryl and C(O)Z;

R$^1$ through R$^4$ are selected independently from H; carboxyl; C$_{1-4}$alkyl; C$_{1-4}$alkyl substituted with a group selected from hydroxyl, amino, sulfhydryl, halogen, carboxyl, C$_{1-4}$alkoxycarbonyl and aminocarbonyl; an alpha carbon side chain of a D- or L-amino acid other than proline; and C(O)Z;

R$^5$ and R$^6$ are selected independently from H; carboxyl; amino; C$_{1-4}$alkyl; C$_{1-4}$alkyl substituted by hydroxyl, carboxyl or amino; and C(O)Z;

R$^7$ is selected from H and a sulfur protecting group; and

Z is selected from hydroxyl, alkoxy, an amino acid residue, and a linking group, the peptide being coupled to the metal chelator by a linking group at Z, and the linking group is selected from the group consisting of —NH—(CH$_2$)$_3$NH— and —NH(CH$_2$)$_2$C(O)NH(CH$_2$)$_2$C(O)NH(CH$_2$)$_2$C(O)NHCH((CH$_2$)$_4$NH—)C(O)NHCH$_2$COOH.

9. A peptide-chelator conjugate according to claim 1, in a form complexed with a diagnostically useful metal or an oxide or nitride thereof.

10. A peptide-chelator conjugate according to claim 5, in a form complexed with a diagnostically useful metal or an oxide or nitride thereof.

11. A peptide-chelator conjugate according to claim 1, selected from a conjugate of Formula (IA) or (IB):

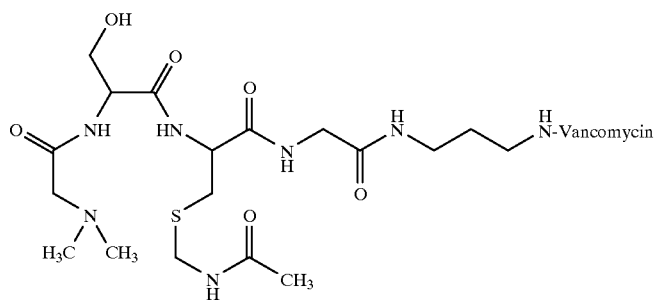

(IA)

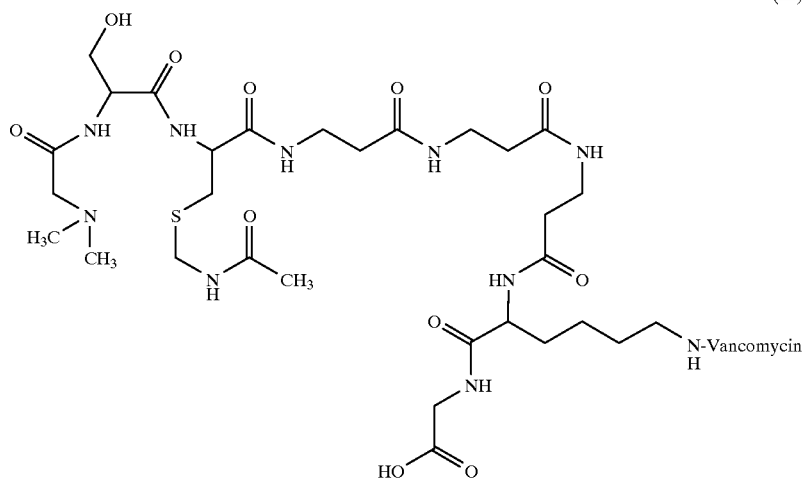

(IB)

12. A peptide-chelator conjugate according to claim 11, in a form complexed with a diagnostically useful metal or an oxide or nitride thereof.

13. A method of imaging a site of inflammation in a mammal comprising the step of administering a diagnostically effective amount of a composition comprising a glycopeptide-chelator conjugate comprising a metal chelator coupled to a glycopeptide antibiotic, the glycopeptide-chelator conjugate in a form complexed with a diagnostically useful metal or an oxide or nitride thereof, the glycopeptide-chelator conjugate being selected from a conjugate of Formula (IA) or (IB):

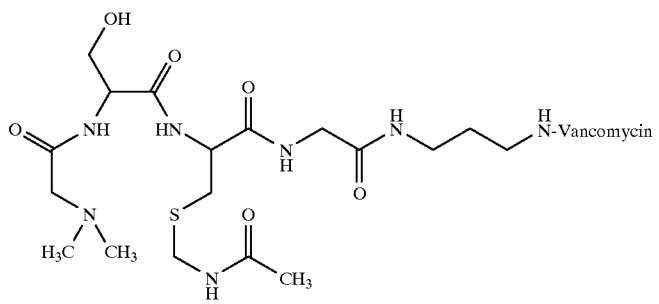

(IA)

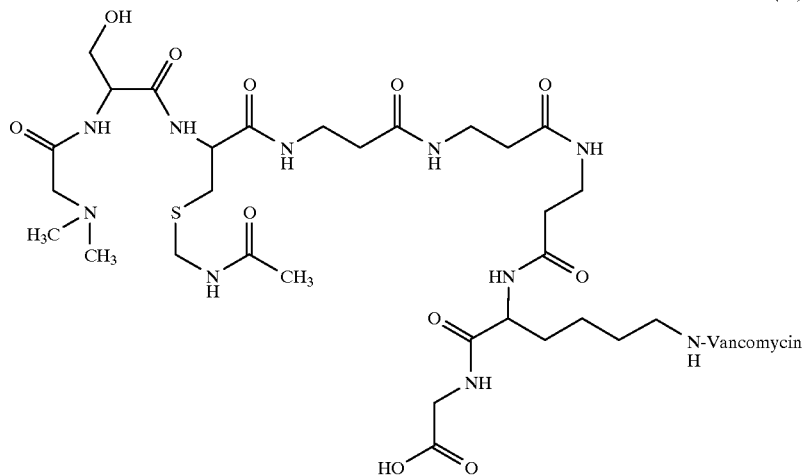

(IB)

14. A peptide-chelator conjugate according to claim 4, wherein the metal chelator has the general Formula (I):

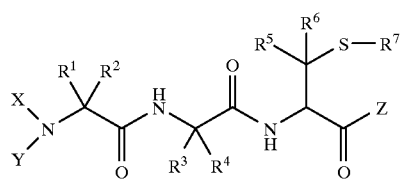

(I)

wherein

X is a linear or branched, saturated or unsaturated $C_{1-4}$alkyl chain that is optionally interrupted by one or two heteroatoms selected from N, O and S; and is optionally substituted by at least one group selected from halogen, hydroxyl, amino, carboxyl, $C_{1-4}$alkyl, aryl and C(O)Z;

Y is H or a substituent defined by X;

X and Y may together form a 5- to 8-membered saturated or unsaturated heterocyclic ring optionally substituted by at least one group selected from halogen, hydroxyl, amino, carboxyl, oxo, $C_{1-4}$alkyl, aryl and C(O)Z;

$R^1$ through $R^4$ are selected independently from H; carboxyl; $C_{1-4}$alkyl; $C_{1-4}$alkyl substituted with a group selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z;

$R^5$ and $R^6$ are selected independently from H; carboxyl; amino; $C_{1-4}$alkyl; $C_{1-4}$alkyl substituted by hydroxyl, carboxyl or amino; and C(O)Z;

$R^7$ is selected from H and a sulfur protecting group; and

Z is selected from hydroxyl, alkoxy, an amino acid residue, and a linking group.

* * * * *

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine
<220> FEATURE:
<221> NAME/KEY: MOD_RES
<222> LOCATION: (3)
<223> OTHER INFORMATION: Modified with an acetamidomethyl group.
<220> FEATURE:
<221> NAME/KEY: MOD_RES
<222> LOCATION: (4)
<223> OTHER INFORMATION: Modified with  3-aminopropylamino Vacomycin.
```

```
<220> FEATURE:
<223> OTHER INFORMATION: Description of Artificial Sequence: Made in
      laboratory

<400> SEQUENCE: 1

Gly Ser Cys Gly
        1

<210> SEQ ID NO 2
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine
<220> FEATURE:
<221> NAME/KEY: MOD_RES
<222> LOCATION: (3)
<223> OTHER INFORMATION: Modified by an Acetamidomethyl group.
<220> FEATURE:
<223> OTHER INFORMATION: Description of Artificial Sequence: Made in
      laboratory

<400> SEQUENCE: 2

Gly Ser Cys Gly
        1

<210> SEQ ID NO 3
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine
<220> FEATURE:
<221> NAME/KEY: MOD_RES
<222> LOCATION: (3)
<223> OTHER INFORMATION: Modified with an Acetamidomethyl group.
<220> FEATURE:
<221> NAME/KEY: MOD_RES
<222> LOCATION: (4)
<223> OTHER INFORMATION: Modified with a 3-aminopropylamino group.
<220> FEATURE:
<223> OTHER INFORMATION: Description of Artificial Sequence: Made in
      laboratory

<400> SEQUENCE: 3

Gly Ser Cys Gly
        1

<210> SEQ ID NO 4
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine
<220> FEATURE:
<221> NAME/KEY: MOD_RES
<222> LOCATION: (3)
<223> OTHER INFORMATION: Modified with an acetamidomethyl group.
<220> FEATURE:
<221> NAME/KEY: MOD_RES
<222> LOCATION: (4)
<223> OTHER INFORMATION: Beta alanine.
<220> FEATURE:
<221> NAME/KEY: MOD_RES
<222> LOCATION: (5)
<223> OTHER INFORMATION: Beta alanine.
<220> FEATURE:
<221> NAME/KEY: MOD_RES
```

```
<222> LOCATION: (6)
<223> OTHER INFORMATION: Beta alanine.
<220> FEATURE:
<221> NAME/KEY: MOD_RES
<222> LOCATION: (7)
<223> OTHER INFORMATION: Vancomycin attached to the tertiary N.
<220> FEATURE:
<223> OTHER INFORMATION: Description of Artificial Sequence: Made in
      laboratory

<400> SEQUENCE: 4

Gly Ser Cys Ala Ala Ala Lys Gly
       1               5

<210> SEQ ID NO 5
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: Modified with a t-Butyl group.
<220> FEATURE:
<221> NAME/KEY: MOD_RES
<222> LOCATION: (3)
<223> OTHER INFORMATION: Modified with an acetamidomethyl group.
<220> FEATURE:
<221> NAME/KEY: MOD_RES
<222> LOCATION: (4)
<223> OTHER INFORMATION: Beta alanine.
<220> FEATURE:
<221> NAME/KEY: MOD_RES
<222> LOCATION: (5)
<223> OTHER INFORMATION: Beta alanine.
<220> FEATURE:
<221> NAME/KEY: MOD_RES
<222> LOCATION: (6)
<223> OTHER INFORMATION: Beta alanine.
<220> FEATURE:
<221> NAME/KEY: MOD_RES
<222> LOCATION: (8)
<223> OTHER INFORMATION: Modified with a sarsin resin.
<220> FEATURE:
<223> OTHER INFORMATION: Description of Artificial Sequence: Made in
      laboratory

<400> SEQUENCE: 5

Gly Ser Cys Ala Ala Ala Lys Gly
       1               5

<210> SEQ ID NO 6
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: Modified with a t-Butyl group.
<220> FEATURE:
<221> NAME/KEY: MOD_RES
<222> LOCATION: (3)
<223> OTHER INFORMATION: Modified with an acetamidomethyl group.
<220> FEATURE:
<221> NAME/KEY: MOD_RES
<222> LOCATION: (4)
<223> OTHER INFORMATION: Beta alanine.
<220> FEATURE:
<221> NAME/KEY: MOD_RES
```

```
<222> LOCATION: (5)
<223> OTHER INFORMATION: Beta alanine.
<220> FEATURE:
<221> NAME/KEY: MOD_RES
<222> LOCATION: (6)
<223> OTHER INFORMATION: Beta alanine.
<220> FEATURE:
<221> NAME/KEY: MOD_RES
<222> LOCATION: (7)
<223> OTHER INFORMATION: Modified by a Dde group.
<220> FEATURE:
<221> NAME/KEY: MOD_RES
<222> LOCATION: (8)
<223> OTHER INFORMATION: Modified by a sarsin residue.
<220> FEATURE:
<223> OTHER INFORMATION: Description of Artificial Sequence: Made in
      laboratory

<400> SEQUENCE: 6

Gly Ser Cys Ala Ala Ala Lys Gly
       1               5

<210> SEQ ID NO 7
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine
<220> FEATURE:
<221> NAME/KEY: MOD_RES
<222> LOCATION: (3)
<223> OTHER INFORMATION: Modified with an acetamidomethyl group
<220> FEATURE:
<221> NAME/KEY: MOD_RES
<222> LOCATION: (4)
<223> OTHER INFORMATION: Beta alanine.
<220> FEATURE:
<221> NAME/KEY: MOD_RES
<222> LOCATION: (5)
<223> OTHER INFORMATION: Beta  alanine.
<220> FEATURE:
<221> NAME/KEY: MOD_RES
<222> LOCATION: (6)
<223> OTHER INFORMATION: Beta alanine.
<220> FEATURE:
<221> NAME/KEY: MOD_RES
<222> LOCATION: (7)
<223> OTHER INFORMATION: Vancomycin attached to the tertiary N.
<220> FEATURE:
<221> NAME/KEY: MOD_RES
<222> LOCATION: (8)
<223> OTHER INFORMATION: Modified with a sarsin residue.
<220> FEATURE:
<223> OTHER INFORMATION: Description of Artificial Sequence: Made in
      laboratory

<400> SEQUENCE: 7

Gly Ser Cys Ala Ala Ala Lys Gly
       1               5

<210> SEQ ID NO 8
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: Modified with a t-Butyl group.
<220> FEATURE:
<221> NAME/KEY: MOD_RES
```

```
<222> LOCATION: (3)
<223> OTHER INFORMATION: Modified with a acetamidomethyl group.
<220> FEATURE:
<221> NAME/KEY: MOD_RES
<222> LOCATION: (4)
<223> OTHER INFORMATION: Beta alanine.
<220> FEATURE:
<221> NAME/KEY: MOD_RES
<222> LOCATION: (5)
<223> OTHER INFORMATION: Beta alanine.
<220> FEATURE:
<221> NAME/KEY: MOD_RES
<222> LOCATION: (6)
<223> OTHER INFORMATION: Beta alanine.
<220> FEATURE:
<221> NAME/KEY: MOD_RES
<222> LOCATION: (7)
<223> OTHER INFORMATION: Vancomycin attached to the tertiary N.
<220> FEATURE:
<223> OTHER INFORMATION: Description of Artificial Sequence: Made in
      laboratory

<400> SEQUENCE: 8

Gly Ser Cys Ala Ala Ala Lys Gly
        1               5

<210> SEQ ID NO 9
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: Modified with a t-Butyl group.
<220> FEATURE:
<221> NAME/KEY: MOD_RES
<222> LOCATION: (3)
<223> OTHER INFORMATION: Modified with an acetamidomethyl group.
<220> FEATURE:
<221> NAME/KEY: MOD_RES
<222> LOCATION: (4)
<223> OTHER INFORMATION: Beta alanine.
<220> FEATURE:
<221> NAME/KEY: MOD_RES
<222> LOCATION: (5)
<223> OTHER INFORMATION: Beta alanine.
<220> FEATURE:
<221> NAME/KEY: MOD_RES
<222> LOCATION: (6)
<223> OTHER INFORMATION: Beta alanine.
<220> FEATURE:
<221> NAME/KEY: MOD_RES
<222> LOCATION: (7)
<223> OTHER INFORMATION: Vancomycin attached to the tertiary N.
<220> FEATURE:
<223> OTHER INFORMATION: Description of Artificial Sequence: Made in
      laboratory
<220> FEATURE:
<221> NAME/KEY: MOD_RES
<222> LOCATION: (8)
<223> OTHER INFORMATION: Modified with a sarsin resin.

<400> SEQUENCE: 9

Gly Ser Cys Ala Ala Ala Lys Gly
        1               5
```